United States Patent [19]

Girard et al.

[11] Patent Number: 5,061,623

[45] Date of Patent: * Oct. 29, 1991

[54] PEPTIDES COMPRISING AN IMMUNOGENIC SITE OF POLIOVIRUS AND DNAS CONTAINING NUCLEOTIDE SEQUENCES CODING FOR THESE PEPTIDES

[75] Inventors: Marc Girard; Sylvie Van Der Werf, both of Paris, France

[73] Assignee: Institut Pasteur, Paris, France

[*] Notice: The portion of the term of this patent subsequent to Nov. 6, 2007 has been disclaimed.

[21] Appl. No.: 538,668

[22] Filed: Jun. 15, 1990

Related U.S. Application Data

[60] Division of Ser. No. 222,392, Jul. 21, 1988, Pat. No. 4,968,627, which is a continuation of Ser. No. 84,932, Aug. 13, 1987, abandoned, which is a division of Ser. No. 634,881, filed as PCT FR83/00241 on Nov. 30, 1983, Pat. No. 4,694,072.

[30] Foreign Application Priority Data

Nov. 30, 1982 [FR] France .................. 82 20115
Jun. 29, 1983 [FR] France .................. 83 10778

[51] Int. Cl.⁵ .................. C12N 15/00; C12P 21/00; C07H 15/12
[52] U.S. Cl. .................. 435/69.3; 435/69.1; 435/320.1; 435/252.3; 435/252.33; 435/255; 536/27; 935/65
[58] Field of Search .............. 536/27; 435/172.3, 69.1, 435/69.3, 235; 935/11, 12, 65

[56] References Cited

U.S. PATENT DOCUMENTS 4,694,071 9/1987 Almonds et al. .................. 435/69.3

FOREIGN PATENT DOCUMENTS 86707 12/1983 European Pat. Off. ......... 435/172.3
82/04067 1/1982 PCT Int'l Appl. .............. 435/172.3
82/03632 4/1983 PCT Int'l Appl. .............. 435/172.3

OTHER PUBLICATIONS

Racaniello, *Proc. Natl. Acad. Sci.*, vol. 78, pp. 4887–4891, Aug. 1981.
Van der werf, *Proc. Natl. Acad. Sci.*, vol. 80, pp. 5080–5089, Aug. 1983.
Nomoto, *Proc. Natl. Acad. Sci.*, vol. 79, pp. 5743–5747, Oct. 1982.

*Primary Examiner*—Robin L. Teskin
*Attorney, Agent, or Firm*—Oblon, Spivak, McClelland, Maier & Neustadt

[57] ABSTRACT

The invention relates to a DNA fragment containing at the most 315 pairs of nucleotides coding for a peptide which can be recognized by antibodies acting both against the "C" and "D" particles of the same poliovirus and against the VP-1 structural polypeptide of the capsid of this poliovirus. This peptide contains in particular the following sequence: Asp Asn Pro Ala Ser Thr Asn Lys Asp Lys Leu.

11 Claims, 12 Drawing Sheets

FIG. 1

```
                                                              2480  2490  2500
                                                              |GGGTTAGGTCAGATGCTTGAA
                                                              VP3 VP1
2510    2520    2530    2540    2550    2560    2570    2580    2590    2600
AGCATGATTGACAACACAGTCCGTGAAACGGTGGGGCGGCAACATCTAGAGACGCTCTCCCAAACACTGAAGGCAGTGGACCAACACACTCCAAGGAAA
                                        XBA1

2610    2620    2630    2640    2650    2660    2670    2680    2690    2700
TTCCGGCACTCACCGCAGTGGAAACTGGGGCCACAAATCCACTAGTCCCTTCTGATACAGTGCAAACCAGACAGTGTTGTACAAGATAGGTCAAGGTCAGA
HPA11             HAE111                                                    RSA1

2710    2720    2730    2740    2750    2760    2770    2780    2790    2800
GTCTAGCATAGAGTCTTTCTTGGGCCGGGGTGCATGCGTGACCATTATGACCGTGGATAACCCAGCTTCCACCAGAATAAGGATAAGCTATTTGCAGTG
         BCER                                                                           ALU1
         HHA1
         BCER 2810    2820    2830    2840    2850    2860    2870    2880    2890    2900
TGGAAGATCACTTATAAAGATACTGTCCAGTTACGGGAGGAAATTGGAGTTCTTCACCTATTCTAGATTTGATATGGAACTTACCTTTGTGGTTACTGCAA
SAU3A                                                        XBA1

2910    2920    2930    2940    2950    2960    2970    2980    2990    3000
ATTTCACTGAGACTAACAATGGGCATGCCTTAAATCAAGTGTACGTACCACCAGGCGTCCAGTGCCCGAGAAATGGGACGACTACAC
                                     RSA1                HAE11  AVA1
                                                         HHA1

3010    3020    3030    3040    3050    3060    3070    3080    3090    3100
ATGGCAAACCTCATCAAATCCATCAATCTTTTACACCTACGGAACAGCTCCAGCCGGATCTCGGTACCGTATGTTGGTATTTCGAACGCCTATTCACAC
                                       ALU1  HPA11  KPN1     SAU3A  RSA1           ASU11
                                                    RSA1                            TAQ1

3110    3120    3130    3140    3150    3160    3170    3180    3190    3200
TTTTACGACGGTTTTCCAAAGTACCAAGGACCAGTCGGCAGCACTAGGTGACTCCCTTTATGGTGCAGCATCTCTAAATGACTTCGGTATTTTGG
               RSA1
```

```
      3210      3220      3230      3240      3250      3260      3270      3280      3290      3300
CTGTTAGACTAGTCAATGATCACAACCCGACCAAGGTCACCTCCAAAATCAGAGTGTATCTAAAACCCAAACACATCAGAGTCTGGTGCCCGCGTCCACC
                 BCL1                                                                            BCER
                 SAU3A 3310      3320      3330      3340      3350      3360      3370      3380
GAGGGCAGTGGCGTACTACGGCCCTGGAGTGGATTACAAGGATGGTACGCTTACACCCCTCTCCACCAAGGATCTGACCACATAT
     RSA1   HAEIII                       RSA1                              SAU3A       VP1
```

```
                                    2250      2260      2270      2280      2290      2300
                              CTGCAGTCCTCATGTACTATGTAGTGCCATGGATTAGCAACACCACGTATCGGCAAA
                                   PST1           RSA1

2310      2320      2330      2340      2350      2360      2370      2380      2390      2400
CCATAGATGATAGTTCACCGAAGGCGGATACATCAGCGTCTTCTACCAAACTAGAAATAGTCGTCCCTCTTTCGACACCCAGAGAGATGGACATCCTTGG
                                                                                    TAQ1

2410      2420      2430      2440      2450      2460      2470      2480      2490      2500
TTTTGTGTCAGCGTGTAATGACTTCAGCGTGCGCTTGTTGCGAGATACCACCACATATAGAGCAAAAGCCGCTAGCACAGGGGTTAGGTCAGATGCTTGAA
                 HHA1                                              HAE11           VP3 VP1
                                                                   HHA1

2510      2520      2530      2540      2550      2560      2570      2580      2590      2600
AGCATGATTGACAACAGAGTCCGTGAAACGGTGGGGCGGCAACATCTAGAGACGCTCTCCCAAAACACTGAAGCCAGTGGACCAACACACTCCAAGGAAA
                                          XBA1

His
                                                                              (65)
  2610      2620      2630      2640      2650      2660      2670      2680      2690      2700
TTCCGGCACTCACCGGCAGTGAAAACTGGGGCCACAAATCCACTAGTCCCTTCTGATACAGTGCAAACCAGACATGTGTACAAGATAGGTCAAGGTCAGA
  HPA11                        HAE111                                              RSA1

Phe
                                                                                       (105)
  2710      2720      2730      2740      2750      2760      2770      2780      2790      2800
GTCTAGCATAGAGTCTTTCTTCGGCGGGGGTGCATGCTGTGACCATTATGACCGTGGATAACCCAGCTTCCACCAGGATAAGGATAAGCTATTGCAGTG
   BCER                                                                                   ALU1
   HHA1
   BCER 2810      2820      2830      2840      2850      2860      2870      2880      2890      2900
TGGAAGATCACTTATAAAGATACTGTCCAGTTACGGAGGAAATTGGAGTTCTTCACCTATTCTAGATTTGATATGGAACTTACCTTGTGGTTACTGCAA
   SAU3A                                                            XBA1
```

```
2910       2920       2930       2940       2950       2960       2970       2980       2990       3000
ATTTCACTGAGACTAACAATGGGCATGCCTTAAATCAAGTGTACCAAATTATGTACGTACCACCAGGCGCTCCAGTGCCCGAGAAATGGGACGACTACAC
                                        RSA1        RSA1        HAE11       AVA1
                                        RSA1                    HHA1

3010       3020       3030       3040       3050       3060       3070       3080       3090       3100
ATGGCAAACCTCATCAAATCCATCAATCATCAATCTTTTACACCTACGGAACAGTCCAGCCCGGATCTCGGTACCGTATGTGGTATTCGAACGCCTATTCACAC
                            ALU1        HPA11     KPN1                        ASU11
                                        SAU3A    RSA1                          TAQ1

3110       3120       3130       3140       3150       3160       3170       3180       3190       3200
TTTTACGACGGTTTTTCCAAAGTACCACTGAAGGAGACCAGTCGGCAGCACTAGGTGACTCCCTTATGGCAGCATCTCTAAATGACTTCGGTATTTTGG
RSA1

3210       3220       3230       3240       3250       3260       3270       3280       3290       3300
CTGTTAGAGTAGTCAATGATCACAACCCGACCAAGGTCACCTCCAAAATCAGAGTGTATCTAAAACCCAAACACATCAGAGTCTGGTGCCCGTCCACC
            BCL1                                                                                  BCER
            SAU3A 3310       3320       3330       3340       3350       3360       3370       3380       3390       3400
GAGGCAGTGGCGTACGTACGGCCCTGAGAGTGGATTACAAGGATGTACGCTTACACCCCTCTCCACCAAGGATCTGACCACATAGGATTCGGAACCAA
RSA1        HAE111                                      RSA1                            SAU3A       VP1

3410       3420
AACAAAGGGGTGTACACTGCAGG
RSA1 PST1
```

FIG. 4

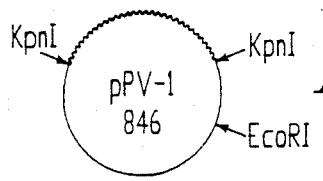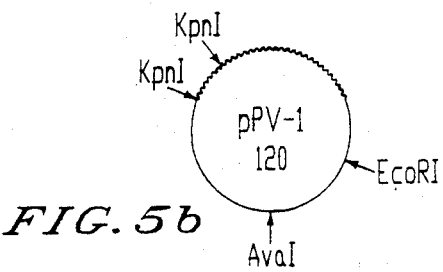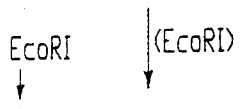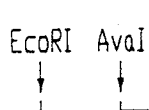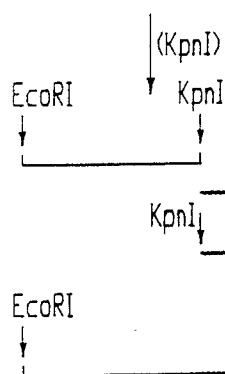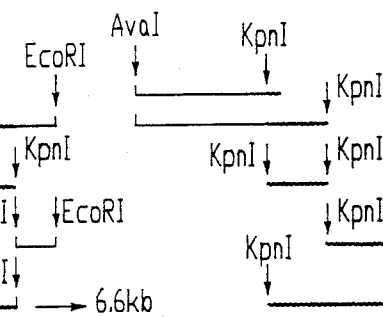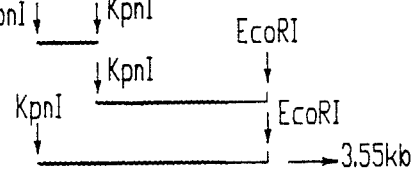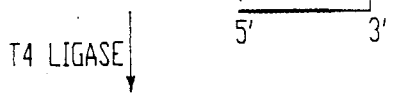

```
         LEU GLN SER CYS THR MET VAL VAL PRO TRP ILE SER ASN THR THR TYR ARG GLN THR
         CTG CAG TCC TCA TGT ACT ATG GTA GTG CCA TGG ATT AGC AAC ACC ACG TAT CGG CAA ACC
    2363 PstI
         ILE ASP ASP SER PHE THR GLU GLY GLY TYR ILE SER VAL PHE TYR GLN THR ARG ILE VAL
         ATA GAT GAT AGT TTC ACC GAA GGC GGA TAC ATC AGC GTC TTC TAC CAA ACT AGA ATA GTC
    2363
         VAL PRO LEU SER THR PRO ARG GLU MET ASP ILE LEU GLY PHE VAL SER ALA CYS ASN ASP
         GTC CGT CTT TCG ACA CCC AGA GAG ATG GAC ATC CTT GGT TTT GTG TCA GCG TGT AAT GAC
    2423                                                     ├──VP3
         PHE SER VAL ARG LEU LEU ARG ASP THR HIS ILE GLU GLN LYS ALA LEU ALA GLN│GLY
         TTC AGC GTG CGC TTG TTG CGA GAT ACC CAT ATA GAG CAA AAA GCG CTA GCA CAG│GGG
    2483                                                               VP3──┤├──VP1
         LEU GLY GLN MET LEU GLU SER MET ILE ASP ASN THR VAL ARG GLU THR VAL GLY ALA ALA
         TTA GGT CAG ATG CTT GAA AGC ATG ATT GAC AAC ACA GTC CGT GAA ACG GTG GGG GCG GCA
    2543
         THR│SER ARG│ASP ALA LEU PRO ASN THR GLU ALA SER GLY PRO THR HIS SER LYS GLU ILE
         ACA│TCT AGA│GAC GCT CTC CCA AAC ACT GAA GCC AGT GGA CCA ACA CAC TCC AAG GAA ATT
    2603     XbaI
         PRO ALA LEU THR ALA VAL GLU THR GLY ALA THR ASN PRO LEU VAL PRO SER ASP THR VAL
         CCG GCA CTC ACC GCA GTG GAA ACT GGG GCC ACA AAT CCA CTA GTC CCT TCT GAT ACA GTG
    2663
         GLN THR ARG HIS VAL VAL GLN HIS ARG SER ARG SER GLU SER SER ILE GLU SER PHE PHE
         CAA ACC AGA CAT GTT GTA CAA CAT AGG TCA GAG TCT AGC ATA GAG TCT TTG TTC
    2723
         ALA ARG GLY ALA CYS VAL THR ILE MET THR VAL ASP ASN PRO ALA SER THR THR ASN LYS
         GCG CGG GGT GCA TGC GTG ACC ATT ATG ACC GTG GAT AAC CCA GCT TCC ACC ACG AAT AAG
```

FIG. 8a

```
2783
ASP LYS LEU PHE ALA VAL TRP LYS ILE THR TYR LYS ASP THR VAL GLN LEU ARG ARG LYS
GAT AAG CTA TTT GCA GTG TGG AAG ATC ACT TAT AAA GAT ACT GTC CAG TTA CGG AGG AAA
2843
LEU GLY PHE PHE THR TYR SER ARG PHE ASP MET GLU LEU THR PHE VAL VAL THR ALA ASN
TTG GAG TTC TTC ACC TAT TCT AGA TTT GAT ATG GAA CTT ACC TTT GTG GTT ACT GCA AAT
                          XbaI
2903
PHE THR GLU THR ASN ASN GLY HIS ALA LEU ASN GLN VAL TYR GLN ILE MET TYR VAL PRO
TTC ACT GAG ACT AAC AAT GGG CAT GCC TTA AAT CAA GTG TAC CAA ATT ATG TAC GTA CCA
2963
PRO GLY ALA PRO VAL PRO GLU LYS TRP ASP ASP TYR THR TRP GLN THR SER SER ASN PRO
CCA GGC GCT CCA GTG CCC GAA AAA TGG GAC GAC TAC ACA TGG CAA ACC TCA TCA AAT CCA
3023
SER ILE PHE TYR THR TYR TYR GLY THR ALA PRO ALA ARG ILE SER VAL PRO TYR VAL GLY ILE
TCA ATC TTT TAC ACC TAC TAT GGA ACA GCT CCA GCC CGG ATC TCG GTA CCG TAT GTT GGT ATT
                                                           KpnI
3083
SER ASN ALA TYR SER HIS PHE TYR ASP SER LEU TYR GLY ALA ALA SER LEU ASN ASP PHE GLY ILE LEU LYS ASP GLN SER
TCG AAC GCC TAT TCA CAC TTT TAC GAC TCC CTT TAT GGT GCA GCA TCT CTA AAT GAC TTC GGT ATT TTG GCT
3143
ALA ALA LEU GLY ASP SER LEU TYR GLY ALA ALA SER LEU ASN ASP PHE GLY ILE LEU LYS ASP GLN SER
GCA GCA CTA GGT GAC TCC CTT TAT GGT GCA GCA TCT CTA AAT GAC TTC GGT ATT TTG GCT
3203
VAL ARG VAL VAL ASN ASP HIS ASN PRO THR LYS VAL THR SER LYS ILE ARG VAL TYR LEU
GTT AGA GTA GTC AAT GAT CAC AAC CCG ACC AAG GTC ACC TCC AAA ATC AGA GTG TAT CTA
```

LYS PRO LYS HIS ILE ARG VAL TRP CYS PRO ARG PRO PRO ARG ALA VAL ALA TYR TYR GLY
AAA CCC AAA CAC ATC AGA GTC TGG TGC CCG CGT CCA CCG AGG GCA GTG GCG TAC TAC GGC
3323

PRO GLY VAL ASP TYR LYS ASP GLY THR LEU PRO LEU SER THR PRO LEU SER LYS ASP LEU THR THR
CCT GGA GTG GAT TAC AAG GAT GGT ACG CTT ACA CCC CTC TCC ACC AAG GAT CTG ACC ACA 3383      35      ←――― NCNP3b ―――→
VP1 ↓ TYR | GLY PHE GLY HIS GLN ASN LYS ALA VAL TYR THR ALA GLY TYR LYS ILE CYS ASN TYR
    TAT | GGA TTC GGA CAC CAA AAC AAA GCG GTG TAC ACT GCA GGT TAC AAA ATT TGC AAC TAC
                                              └――― PstI ―――┘
3443

HIS LEU ALA THR GLN ASP ASP LEU GLN GLY THR ASP SER ILE ALA ARG CYS ASN VAL MET TRP SER ARG ASP LEU
CAC TTG GCC ACT CAG GAT GAT TTG CAA GGC ACC GAT TCA ATC GCA AGG TGC AAT GTC ATG TGG AGT AGA GAC CTC
3503

LEU VAL THR GLU SER ARG ARG ALA GLN GLY THR ASP SER ILE ALA ARG CYS ASN ALA
TTA GTC ACA GAA TCA AGA AGG CAG GGT ACC GAT TCA ATC GCA AGG TGC AAT GCA

GLY THR ASP SER ILE ALA ARG CYS ASN ALA
GGC ACC GAT TCA ATC GCA AGG TGC AAT GCA

LYS TYR TYR PRO VAL GLY PRO THR
AAA TAC TAC CCA GTA GGC CCA ACG

GLY VAL TYR TYR CYS GLU SER ARG ARG LYS TYR TYR PRO VAL SER PHE VAL GLY PRO THR
GGG GTG TAC TAC TGC GAG TCT AGA AGG AAA TAC TAC CCA GTA TCC TTC GTT GGC CCA ACG
3563

*FIG. 8c*

PEPTIDES COMPRISING AN IMMUNOGENIC SITE OF POLIOVIRUS AND DNAS CONTAINING NUCLEOTIDE SEQUENCES CODING FOR THESE PEPTIDES

This is a division of application Ser. No. 07/222,392, filed on July 21, 1988 now U.S. Pat. No. 4,968,627 which is a continuation of Ser. No. 07/84,932, filed Aug. 13, 1987; now abandonded, which is a divisional of Ser. No. 06/634,881, filed as PCT FR83/00241 on Nov. 30, 1983, now U.S. Pat. No. 4,694,072.

BACKGROUND OF THE INVENTION

The invention relates to peptides comprising an immunogenic site of poliovirus and DNA fragments containing nucleotide sequences coding for these peptides. The invention also relates to vaccinating principles bringing such peptides into play, these principles being adapted to induce in the host, man or animal, the production of antibodies active not only against themselves, but also against complete infectious polioviruses.

In French Patent Application 82 02013 filed 8 Feb. 1982 there have already been described DNA fragments coding for an immunogenic peptide capable of inducing in vivo the synthesis of antipoliovirus antibodies. These DNA fragments possess a length not exceeding that of a DNA fragment comprising of the order of 1.2 kb (kilopairs of bases). These fragments are more particularly characterized in that they contain a nucleotide sequence coding for the protein VP-1, which has been found to bear essential antigenic determinants brought into play at the level of the immunogenicity of the corresponding infectious poliovirus. In fact, this peptide is capable of forming antigen-antibody complexes with monoclonal or polyclonal neutralizing serums obtained from animals in which whole poliovirus had been injected (serum of D-specificity)

DNA type sequences coding for immunogenic peptides of the above-indicated type are illustrated in the succession of the appended FIGS. 1 and 2, for one of them, and in the succession of FIGS. 3 and 4, also appended, for another DNA fragment containing the abovesaid sequence. The locations of certain restriction sites to which reference will be made below are also indicated in these drawings The numbering of the successive nucleotides taking part in the constitution of these DNAs is effected from the 5' end. With respect to the constitution of the clonable DNA of the poliovirus from which the abovesaid DNAs have been obtained, reference will be made to the article of Sylvie VAN DER WERF and other authors, entitled "Molecular Cloning of the Genome of Poliovirus" in Proc. Nat. Acad. Sci. U.S.A., Vol. 78, No. 10, pp. 59-83, 59-87, October 1981.

The invention arises from the discovery that peptides corresponding to the DNA sequences contained in the preceding ones, but much smaller than the latter, carried nonetheless antigenic determinants enabling their use in the constitution of vaccinating principles effective against the corresponding polioviruses. From the peptides concerned, some can be isolated the size of which is sufficiently small for them to be directly accessible by chemical synthesis.

The invention provides in addition technique enabling the determination, within DNAs of relatively large size which form the subject of French Patent Application No. 82 02013, of those of the smaller DNA sequences to which correspond peptides having determinants or antigenic sites making them suitable for use in the production of vaccinating principles against corresponding whole and infectious polioviruses.

In this regard, the longest of the DNA sequences according to the invention is constituted by the fragment bounded at its opposite ends by XbaI sites located in the regions defined by the positions 2546 and 2861 of FIG. 1.

The invention relates more particularly still to those of the DNA sequences contained within the preceeding one and which code a peptide capable of being recognized by monoclonal antibodies active both against "C" and "D" particles originating from a same poliovirus and against the structural polypeptide VP-1 of the capsid of the same poliovirus. It is this type of monoclonal antibody which is concerned in all circumstances in the description which follows, except when it is otherwise specified.

Such antibodies are obtained from hybridoma which have been obtained by the carrying out of the fusion of spleen cells of an animal previously immunized by a virus or virion having a "C" antigenicity (obtained by thermal treatment for 1 hour at 56° C. of the corresponding infectious poliovirus having "D" antigenicity) and suitable myelomatous cells using a method known per se, by the cultivation of the clones or hybrid cells obtained and by the selection of the clones which are found to produce monoclonal antibodies active both against the virus with "C" antigenicity, the homologous infection viruses (virions) with "D" antigenicity and against the corresponding protein VP-1. The homologous virions contemplated herein are advantageously of the 1-type (Mahoney). Such monoclonal antibodies (denoted hereafter under the expression "CD-VP-1 antibodies (or "C3")), the hybrid cells capable of producing them and a process for their production were described in French Patent Application No. 82 19338 filed on 18 Nov. 1982. Two of the cell hybrids formed have been deposited at the National Culture Collection of Micro-Organisms of the Pasteur Institute of Paris (C.N.C.M.), respectively under no. I-208 and no. I-209.

This sequence according to the invention has the following structure:

```
TCT AGA GAC GCT CTC CCA AAC ACT GAA
GCC AGT GGA CCA ACA CAC TCC AAG GAA ATT
CCG GCA CTC ACC GCA GTG GAA ACT GGG GCC
ACA AAT CCA CTA GTC CCT TCT GAT ACA GTG
CAA ACC AGA CAT GTT GTA CAA CAT AGG TCA
AGG TCA GAG TCT AGC ATA GAG TCT TTC TTC
GCG CGG GGT GCA TGC GTG ACC ATT ATG ACC
GTG GAT AAC CCA GCT TCC ACC ACG AAT AAG
CAT AAG CTA TTT GCA GTG TGG AAG ATC ACT
TAT AAA GAT ACT GTC CAG TTA CGG AGG AAA
TTG GAG TTC TTC ACC TAT TCT
```

The invention also relates to any DNA sequence coding for a peptide having immunogenic properties similar to those of the peptide coded by the abovesaid nucleotide sequence. In particular any triplet of the sequence can be replaced, either by a distinct triplet coding for the same amino acid or for a distinct amino acid, to the extent that the substitution of the second for the first in the peptide coded by the DNA sequence concerned, will not fundamentally alter the immunogenic properties of the peptide coded by the so modified DNA sequence. In particular, the invention relates to any DNA sequence of this type coding for a peptide which can be recognized by the above C3 antibody.

The invention also relates to any nucleotide sequence of smaller length contained in the preceding one, as soon as it codes for a peptide still also capable of being recognized by the C3 antibody.

Among the DNA sequences comprised within the scope of the invention, are included those containing nucleotide sequences coding for the peptide sequence His 65-Phe 105 defined below, and more particularly for the nucleotide sequence 2671-2792 of the gene coding for the polypeptide of VP-1 structure of the poliovirus of FIG. 1.

Other preferred DNA sequences within the field of the invention are those which code for the peptide sequences His 65-Ile110 defined below, and more particularly again the nucleotide sequence Pro 95-Ile110 from the same gene.

The invention relates naturally to the polypeptides containing the peptide sequences coded by the abovesaid DNA sequences. It relates in particular to the sequence of formula:

```
        Ser Arg Asp Ala Leu Pro Asn Thr Glu
    Ala Ser Gly Pro Thr His Ser Lys Glu Ile
    Pro Ala Leu Thr Ala Val Glu Thr Gly Ala
    Thr Asn Pro Leu Val Pro Ser Asp Thr Val
    Gln Thr Arg His Val Val Gln His Arg Ser
    Arg Ser Glu Ser Ser Ile Glu Ser Phe Phe
    Ala Arg Gly Ala Cys Val Thr Ile Met Thr
    Val Asp Asn Pro Ala Ser Thr Thr Asn Lys
    Asp Lys Leu Phe Ala Val Trp Lys Ile Thr
    Tyr Lys Asp Thr Val Gln Leu Arg Arg Lys
    Leu Glu Phe Phe Thr Tyr Ser
```

The invention also relates to any peptide having equivalent immunogenic properties under the conditions which have already been indicated with respect to the peptides coded by the DNA sequences defined above. In this respect the invention relates more particularly to the following sequence, called below "His 65-Phe 105 sequence".

```
                    His Val Val Gln His
    Arg Ser Arg Ser Glu Ser Ser Ile Glu Ser
    70
    Phe Phe Ala Arg Gly Ala Cys Val Thr Ile
    80
    Met Thr Val Asp Asn Pro Ala Ser Thr Thr
    90
    Asn Lys Asp Lys Leu Phe
    100
``` or called below "sequence His 65 - Ile 110".

```
                    His Val Val Gln His
    Arg Ser Arg Ser Glu Ser Ser Ile Glu Ser
    70
    Phe Phe Ala Arg Gly Ala Cys Val Thr Ile
    80
    Met Thr Val Asp Asn Pro Ala Ser Thr Thr
    90
    Asn Lys Asp Lys Leu Phe Ala Val Trp Lys
    100
    Ile
    110
```

The invention relates more particularly also to those of the peptides which contain the following peptide sequence, called below Asp 93-Leu 104: Asp Asn Pro Ala Ser Thr Thr Asn Lys Asp Lys Leu.

The invention relates naturally also to the vectors, particularly of the plasmid or phage type, containing an insert formed by anyone of the DNA sequences such as have been defined above. These modified vectors may be employed in the transformation of cellular organisms or of suitable microorganisms, in order to induce the production by the latter of polypeptides, possibly hybrid ones, containing a peptide sequence recognizable by the CD-PV1 or C3 monoclonal antibodies or other antibodies recognizing the infectious virus. These polypeptides, possibly hybrid ones, also form part of the invention.

The invention provides also a process enabling the identification, within a DNA sequence normally contained within the DNA of a determined poliovirus, of those of the smaller sequences which are capable of coding for an immunogenic peptide or capable of being utilized in the manufacture of an immunogen principle enabling the production of antibodies active against the corresponding whole poliovirus.

This process is essentially characterized in that, starting from a plasmid containing an insert formed of an initial sequence recognized as presumably containing a smaller sequence capable of coding for an immunogenic peptide or a peptide likely of being part of an immunogenic principle, one linearizes said plasmid at the level of a restriction site external to said smaller sequence, one trims the linearized plasmid in controlled manner with an exonucleolytic enzyme, such as enzyme Bal 31, one recircularizes the trimmed plasmid with a DNA ligase, one transforms a suitable microorganism transformable by the corresponding plasmid and capable of expressing the insert contained in the latter, and one detects the possible presence of a peptide liable of bearing the immunogenic site of the type concerned among the expression products of said microorganism, by contacting said expression products with a monoclonal CD-PV1 antibody, said cycle of operations which has been defined being repeated until the disappearance of the detection of said immunogenic peptide among the expression products of the micro-organism as transformed by the last recircularized plasmid.

It is possible, at the end of each of the cycles of the above-defined process, for example, by comparison of the restriction maps of the plasmid before and after the abovesaid trimming operation, to determine those of the DNA sequences which have been removed between two successive trims and, consequently, when the possibility of detection of an immunogeric peptide under the above-indicated conditions ceases, to correlate this result with one of the sequences eliminated in the course of the preceding trimming operation, this eliminated DNA sequence participating in the coding for said immunogenic peptide. The structure of the eliminated sequence (or of the eliminated sequences), may of course result of determinations of terminal nucleotide sequences, before and after the trimming concerned respectively.

Such a principle will be illustrated in one of the examples of practising the invention whose description follows. Reference will also be made in the following to the drawings in which:

FIGS. 1 to 4 correspond to sequences already defined in the foregoing;

FIGS. 5a to 5h show diagrammatically a production mode for a precursor obtained from the clones pPV1-846 and pPV1-120 described in the article of Sylvie VAN DER WERF et al already mentioned above;

FIG. 8 is an additional representation of the sequence coding for VP1, preceded by a portion of the sequence coding for VP3 and followed by a portion of the sequence coding for NCVP3b. This sequence only differentiates essentially from the corresponding portions of sequences appearing in FIGS. 1 to 4 by the numbering of the nucleotides. This numbering conforms with that resulting from the "consensus" to which A. J. DORNER et al refer in the article entitled: "Identification of the Initiation Site of Poliovirus Polyprotein Synthesis" (Journal of Virology, June 1982, Vol. 42, No. 3, pp. 1,017 to 1,028.

This publication refers back to the MOLGEN project of the SUMEX AIM system of Stanford University as regards the relationships to be established between the numbering of the fully published sequences and the numbering adopted in FIG. 8.

Figure 9:
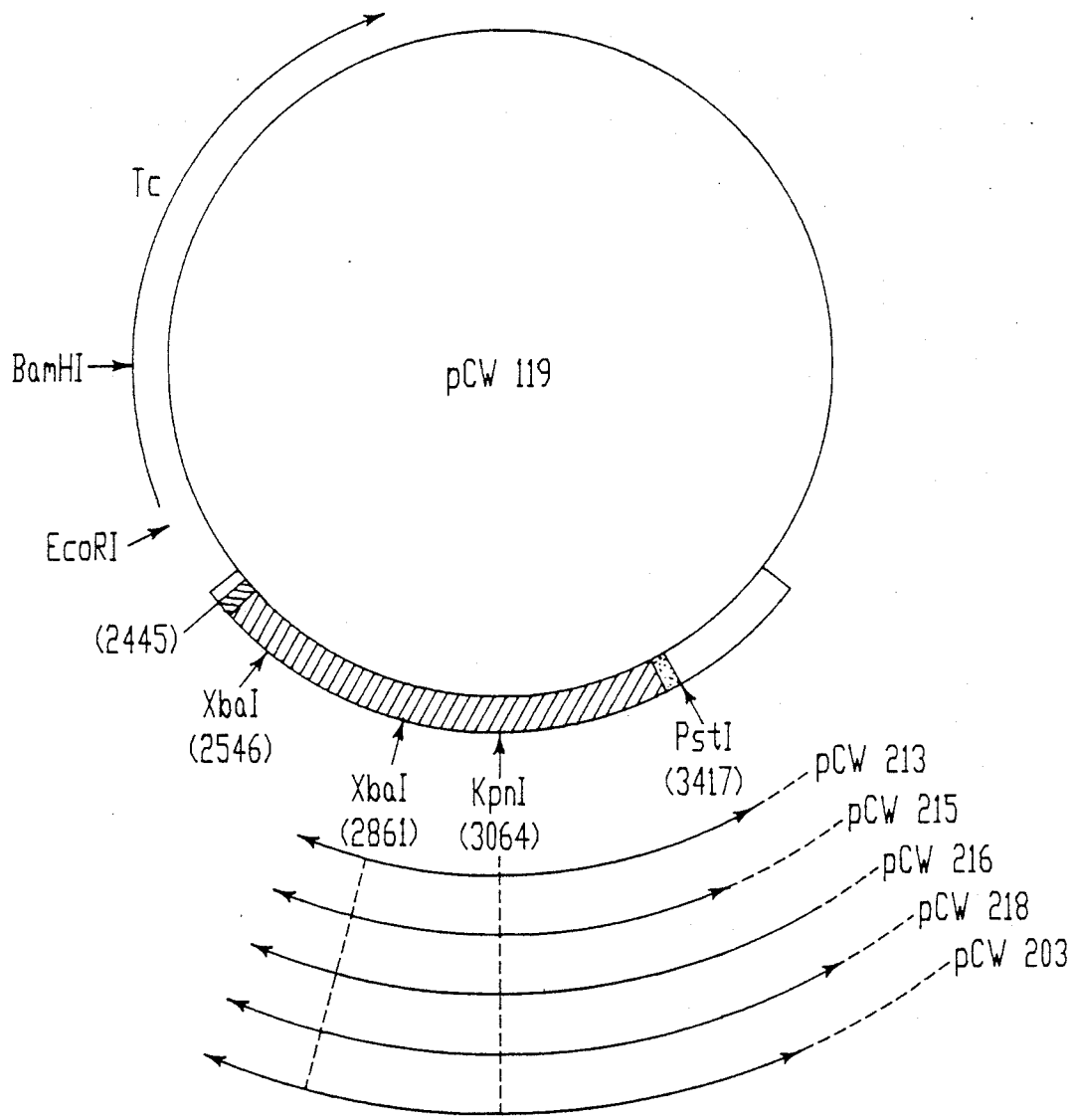

FIG. 9 is a diagrammatic representation of the plasmid pCW 119. It illustrates the relative positions of the deletions introduced in other plasmids discussed below and derived of pCW 119.

Figure 10:
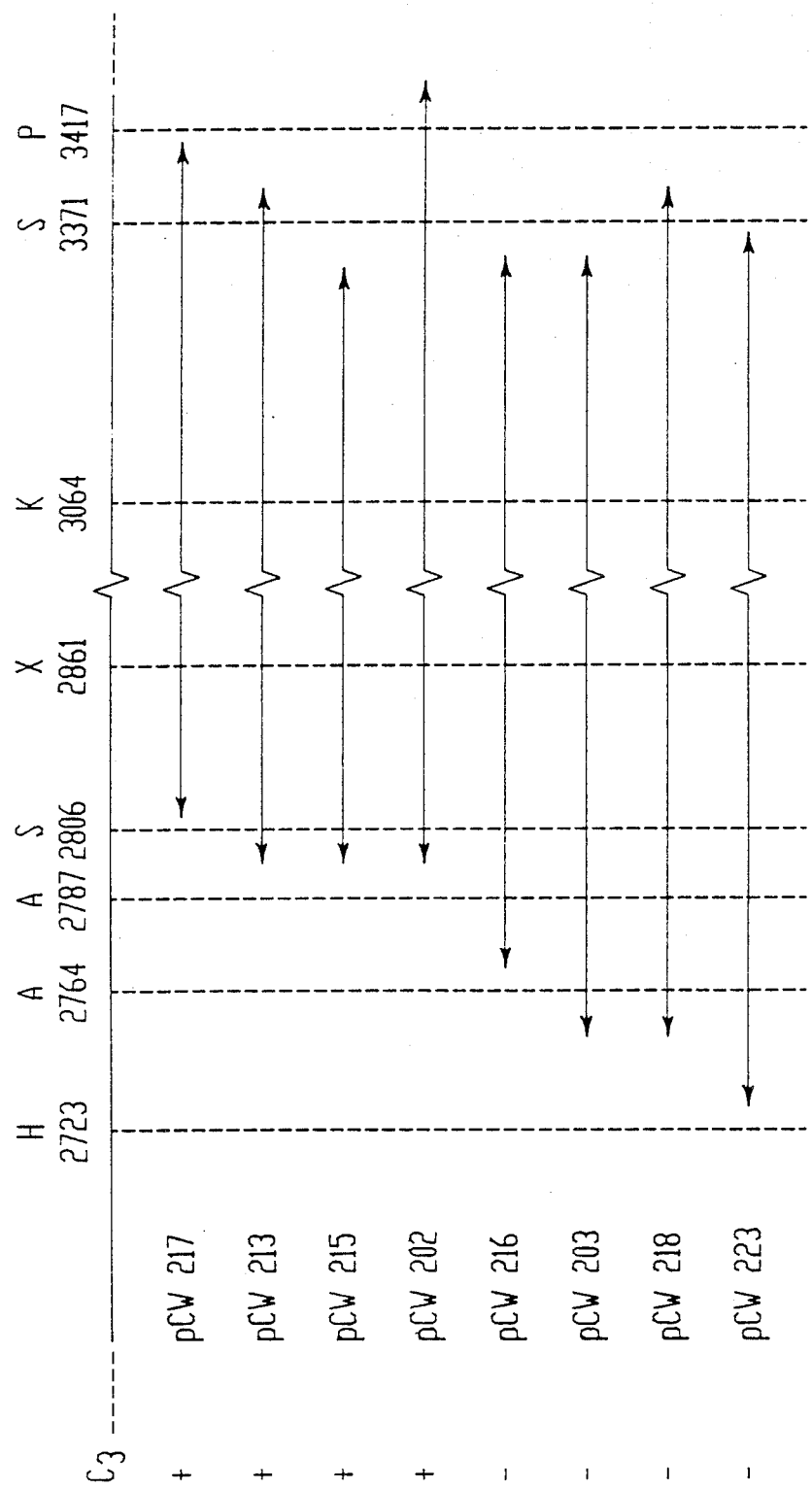

FIG. 10 illustrates more specifically still the positions of these deletions with respect to certain restriction sites in the plasmid pCW 119.

The techniques for the construction of the different plasmids are conventional. The plasmid DNAs have been cleaved each time by restriction enzymes under the conditions provided by their respective manufacturers. The DNA fragments have been analyzed by electrophoresis in an agarose or a polyacrylamide gel. The projecting ends 3' have been transformed into blunt ends by incubation of the DNA fragments (0.1 mg/ml) with 100 μ/ml of DNA I polymerase (Klonow fragment) of E. coli for 1 hour at 37° C. in a 10 mM Tris-HCl medium, pH 7.5 containing 10 mM MgCl₂, 50 mM NaCl, 1 mM DTT in the presence of 0.2 mM of the first nucleotide pairs. The digestion with nuclease Bal 31 was carried out in a 20 mM CaCl₂, 12 mM MgCl₂ medium, by employing an enzyme/DNA ratio of 0.12 u per μg. After incubation for 15 minutes at 30° C., EDTA was added until a concentration of 50 mM was reached and the DNA was extracted wityh phenol and precipitated with ethanol. The ligation reactions were carried out in 20 μl of a 60 mM Tris-HCl medium, pH 7.5, 10 mM MgCl₂, 10 mM DTT, 1 mM ATP for 18 hours at 15° C., by using 1 u of T4 DNA Ligase per μg of DNA. The linearized plasmids have, as the case may be, been treated for 30 min. at 68° C. with a bacterial alkaline phosphatase (0.02 u per μg DNA) before ligation with the appropriate fragments.

1. Hydrolysis of the cloned DNAs by restriction enzymes 1.1 The DNA of plasmid pPVI-846 was hydrolyzed completely by EcoRI. The linear form of the plasmidic DNA so obtained (FIG. 5c) was hydrolized by partial digestion with Kpn I; the fragments obtained (FIG. 5d) were separated by electrophoresis on 0.7% agarose gel.

The fragment of 6.6 kbp size was selected. It represented in fact the sequence of the plasmid pBR322 from the EcoRI site to the Pst I site, extended from that of the DNA corresponding to the sequence of the poliovirus which extends from the nucleotide 1 to the nucleotide 3064 (2nd Kpn I site).

1.2 The DNA of clone pPVI-120 was hydrolized by complete digestion with AvaI and EcoRI thereby forming two fragments of different sizes (FIG. 5e). The DNA was then partially hydrolized by Kpn I. The fragments so obtained (FIG. 5f) were separted by electrophoresis on 0.7% agarose gel.

The fragment of 3.55 kbp size was selected. It represented in fact the sequence of the cDNA of the poliovirus ranging from the nucleotide 3064 (2nd Kpn.I site) to the nucleotide 5650 approximately, extended from that of the 752 pairs of bases of the segment Pst-I-EcoRI of plasmid pBR322.

2. Extraction of the DNA fragments from the gels 2.1 The fragments were made visible in the gels by dyeing with ethidium bromide; those of the desired size were extracted from the gels by electroelution in a dialysis bag.

2.2 The material so obtained was purified and concentrated.

3. Rebonding of the fragments (recombination)

The two selected fragments derived from the clones pPVI-846 and pPVI-120 and described above were mixed and rebonded by means of DNA ligase of phage T4. The sticky ends formed at the cleavage points by EcoRI and KpnI and carried by each end of the two fragments facilitated their rebonding and ensured that the latter was only achieved in the desired direction (FIGS. 5g and 5h).

The genome of plasmid pBR322 was thus reconstituted without modification or deletion in the recombinant plasmid. In particular, the regions necessary for its replication and for the expression of the resistance to tetracycline were not affected.

4. Transformation of the E. coli 1106 strain

The fragments of the plasmids pPVI-846 and -120 bonded by their Kpn I and EcoRI sites were contacted with competent bacteria of the E. coli 1106 strain under the transformation conditions. The colonies of bacteria resistant to tetracyclin and sensitive to ampicillin were selected.

5. Analysis of the new clones 5.1 The plasmidic DNA of the tetracycline resistant bacteria was purified. Its mass was determined by electrophoresis on agarose gel. It was equal to that of the plasmid pBR322 increased by the 5650 pairs of bases of the viral cDNA formed by recombination.

5.2 The in vitro hybridation of the cDNA so obtained with specific probes derived from the clones pPVI-846 and pPVI-120 enabled verification of the presence in a single recombinant clone of the genetic material of the poliovirus inserted originally in the two parent clones.

5.3 Detailed analysis of the new clones was carried out by the methods used previously for studying the clones already characterized (physical mapping by restriction enzymes, electron microscopy, nucleotidic sequence, etc.).

5.4 The cDNA borne by the recombinant plasmid (pPV1-X) or pPV1-958 bore the genetic information necessary for the synthesis of the protein NCVP1a (or P1), precursor of the capsid VP4 proteins (nucleotides 743 to 950) VP2 (nucleotides 951 to 1766), VP3 (1767 to 2479) and VP1 (2480 to 3385), followed by those which correspond to the protein NCVP3b (or P2) (precursor particularly of the protein NCVPX) and at the beginning of the protein NCVP1b (or P3) The whole covers about 5650 of the 7440 bases of the viral genome.

Plasmid pPVI-846 has been deposited at the C.N.C.M. under number I-155 and plasmid 120 under number I-156 on 19 May 1981.

The pPVI-958 plasmid obtained contained in its insert the nucleotide sequence which codes for the proteins VPO (nucleotides 743 to 1766), VP3 (nucleotides 1767 to 2479) and VPI (nucleotides 2480 to 3385) followed by the sequence coding for the protein NCVP3b (nucleotides 3386 to 5100 and some) and of the beginning of that of the protein NCVP1b.

Starting from the plasmid pPVI-958, it was possible to obtain a fragment of cDNA coding for VP1 by proceding as follows.

ISOLATION AND RECLONING OF A cDNA FRAGMENT CONTAINING THE VP1 SEQUENCE

The nucleotide sequence which codes for the protein VP1 is surrounded in the viral genome, and consequently also in the insert borne by pPV1-958, by two PstI sites, located respectively 237 nucleotides upstream (position 2243) and 32 nucleotides downstream (position 3417) from the first and from the last nucleotide of this sequence (cf. restriction map in the above-said publication and FIGS. 1 and 2).

Figure 6A:
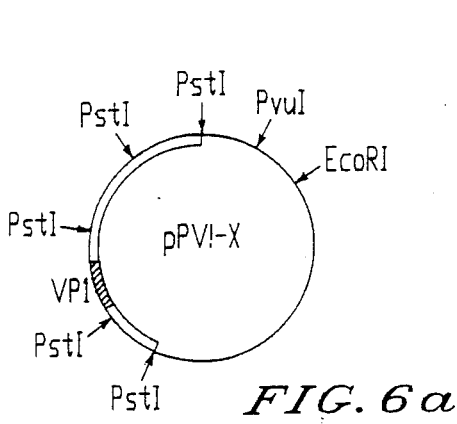
FIGS. 6a to 6f show diagrammatically the steps of a production mode of a plasmid containing the essentials of the genetic information of the DNA sequence resulting from FIGS. 1 and 2.

The cleavage of pPV1-958 (FIG. 6a) by the PstI restriction enzyme hence generates a family of fragments having lengths corresponding respectively to 4.36 kb (body of the plasmid) and to 1.8 kb; 0.43 kb; 1.17 kb and about 2.23 kb. The 1.17 kb fragment bears the nucleotide sequence coding for the end of VP3 and the whole of VPI. The latter fragment starts with the nucleotide sequence 5'G T C C T C A T G T A and terminates by the sequence G T A C A C T G C A3'. It is separated from the other PstI fragments by electrophoresis on agarose gel. The gel strip which contained it was taken up, and subjected to electroelution to extract the DNA therefrom. The electroelution was followed by illumination with ultraviolet light after dyeing the gel with ethidium bromide. The fragment so prepared corresponded to the nucleotides of the poliovirus 2243 to 3417. It was inserted by ligation with DNA-ligase at the PstI site of the vector plasmid pBR-322 previously linearised by this same enzyme. The recombinant plasmids which have thus been formed were cloned in the strain 1106 of *Escherichia coli* (selection of colonies which have become resistant to tetracycline but remain sensitive to ampicillin after transformation by the plasmid).

Analysis of their DNA by mapping with restriction enzymes enabled the identification and selection of the recombinant plasmids which carried the fragment of the polioviral cDNA inserted in the anticlockwise direction with respect to the map of pBR-322, that is to say in the same transcriptional direction as the gene of β-lactamase (gene of resistance to ampicillin). It must be noted that the insertion of the fragment 2243-3417 at the PstI site of pBR-322 interrupts the continuity of the nucleotide sequence, and hence inactivates the gene of β-lactamase of the vector, however does not permit the expression of the polioviral proteins to be ensured since it results in a shift in the reading phase of the insert.

Figure 6B:
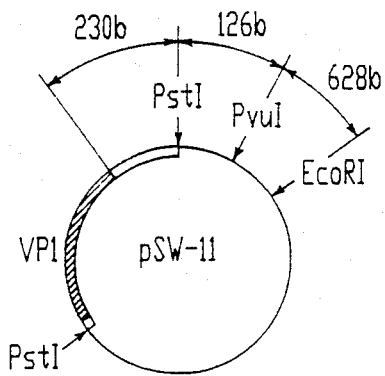

The plasmid having these properties was named pSW-11 (FIG. 6b).

ELIMINATION OF THE SEQUENCES CODING FOR THE TERMINAL PORTION PORTION C OF VP3: TRIMMING OF VP1

Figure 6C:
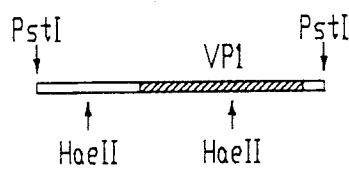

Plasmid pSW-11 contains, preceding, in the transcriptional direction 5→3', the sequence of VP1, 237 nucleotides of cDNA of poliovirus corresponding to part of the VP3 sequence. These nucleotides in excess can be removed in at least two ways:

a) by controlled treatment of the fragment PstI (previously extracted from pSW 11: FIG. 6c) of 1.17 kb by the restriction enzyme HaeII (partial digestion at the level of nucleotide 2467), then selection by electrophoresis of the fragment HaeII-PstI of 0.95 kb (FIG. 6d) (polioviral nucleotides 2467 to 3417) and recloning of this fragment in the appropriate plasmids. It is possible to facilitate the recloning by attaching in a manner known per se to the ends of the trimmed fragment synthetic linkers, i.e. short sequences of nucleotides containing determined restriction sites obtained by synthesis, for example by the technique described by R. H. SCHELLER et al, Science, volume 196 (1977), pp. 177-180. The linker selected depends essentially on the cleavage site of the restriction enzyme used in the expression vector.

b) by linearization of the plasmid pSW-11 by complete digestion by the enzyme PvuI, followed by an exonucleolytic treatment with the enzyme Bal 31 and recirculation of the plasmid by DNA ligase, after addition whenever required of synthetic linkers, such as manufactured by Biolabs, Collaborative Research.

Figure 6E:
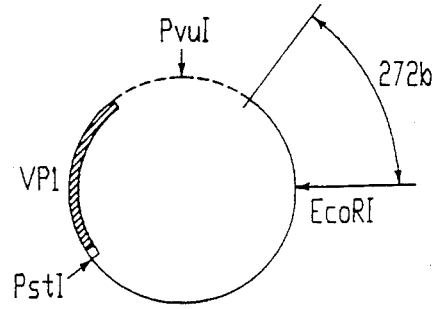
Figure 6D:
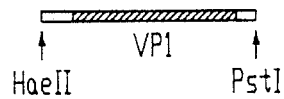

Hence the molecules are opened. Their sizes can be analyzed after electrophoretic migration thereof in agarose gel to identify those which have lost about 700 pairs of bases (loss which in FIG. 6e is symbolized by a circular arc in dashed lines), that is to say some 350 pairs on each side of the PvuI site, namely the PvuI-PstI fragment of pBR-322 plus the sequence of VP3 up to VP1, on the one hand, and a similar length of pBR-322 directed from PvuI towards EcoRI, on the other hand.

In this manner, it is possible to isolate a fragment one end of which coincides with the end of the DNA sequence coding for VP1, or is very close thereto.

In fact, the PvuI site occurs at 126 pairs of bases (b) from the proximal site PstI of the sequence of the PstI fragment of 1.17 kb and at 363 pairs of bases from the proximal end of the fragment of cDNA coding for VP1, in plasmid pSW-11.

Figure 6F:
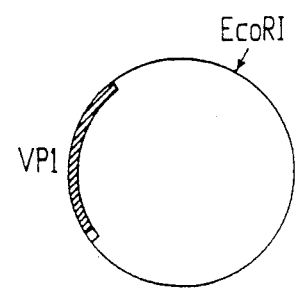

After fixing to the ends of the selected fragment of linkers containing a BglII site by means of a ligase if appropriate, plasmids can be selected the sizes of which are from 4.8 to 5 kb (FIG. 6f). Then those of the plasmids in which the whole VP1 sequence has been preserved, whilst having lost all or almost all VP3, are determined. This can be achieved by determining the nucleotide sequence of the BglII-PstI of the selected plasmids. The fragments to be sequenced can be inserted in the replicative form of the phage M13 and the recombinant phages so constituted be cloned. The cloned DNA-fragment inserted therein can be sequenced by the SANGER technique. The nucleotide sequence can also be determined by the MAXAM and GILBERT method.

The plasmid obtained by trimming the plasmid pSW-11, particularly according to the alternative b of the process described above, yet without the introduction of linker BglII, has been named pSW-119.

Figure 7:
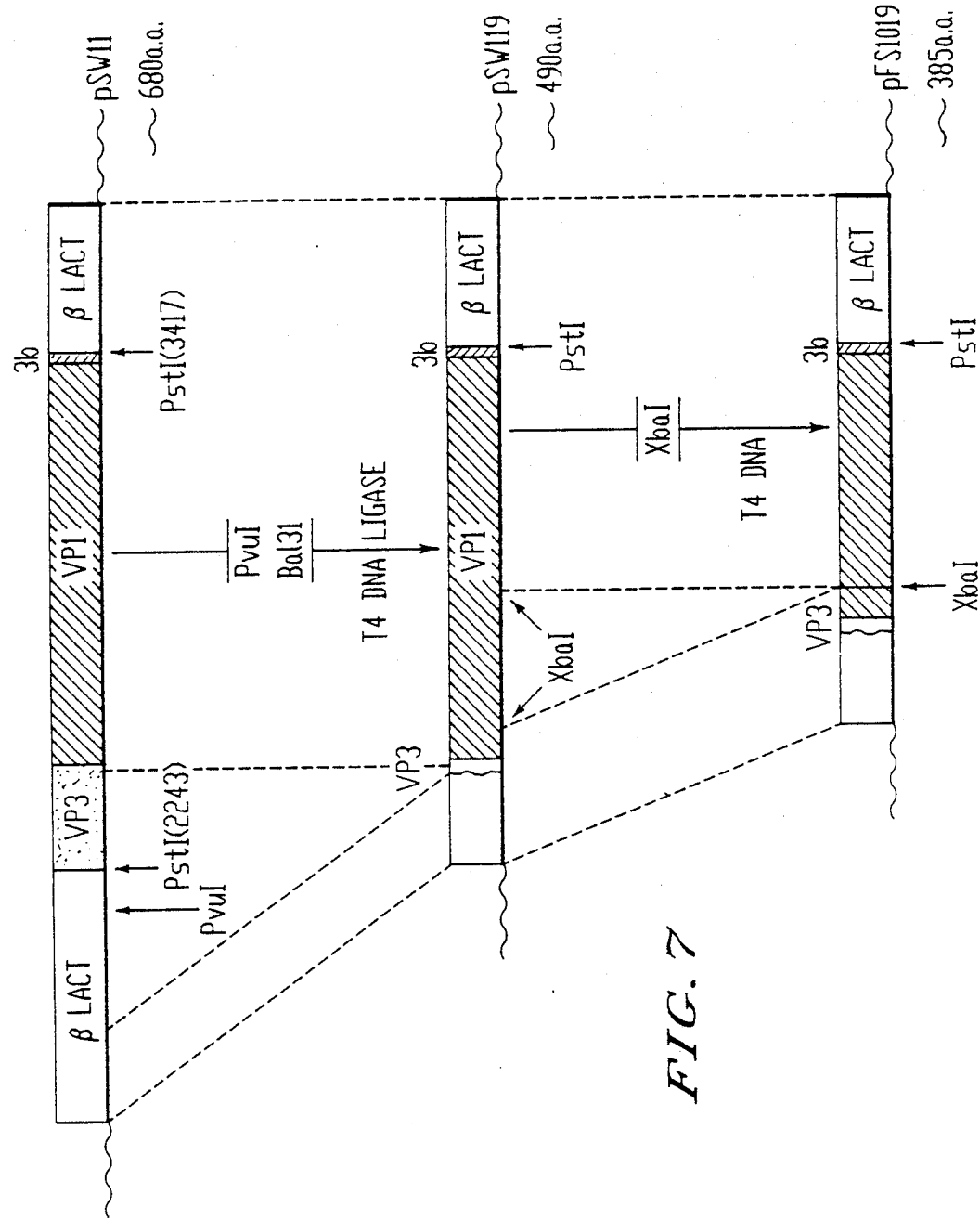
FIG. 7 is a diagrammatic representation of the production of the preceding plasmid and of an additional step brought into play in a first step of the present invention, as will result from the description which follows.

The differences observed between the plasmids pSW-11 and pSW-119 (or pCW-119) result from the diagram of FIG. 7. In particular, the plasmid pSW-119 has lost the greatest part of the sequence which was contained in plasmid pSW-11 and which codes for the VP3 polypeptide structure of the poliovirus.

As has been indicated in French patent application no. 82 02013, plasmid pSW-119 is capable of expressing a fusion protein VP1-$\beta$-lactamase in strains of *E. coli* 1106 or GC 26 (among other micro-organisms, such as those envisaged in prior patent application no. 82 02013). This fusion protein, having a molecular weight of 49,000 daltons, is specifically immunoprecipitated by the monoclonal antibodies CD-VP1 (or C3).

A derivative of pSW-119, pFS119, has been constructed by replacing sequences between the sites BamHI and PstI of pBR 322 (nucleotides 375-3 608) by the corresponding sequences of pBR 327. After labelling of the proteins expressed by the plasmid pFS 119 in bacteria GC 26 with ($^{35}$ S) methionine, immunoprecipitation and analysis by electrophoresis on polyacrylamide gel, it has again been possible to detect a fusion protein having a molecular weight of the order of 49,000 daltons (p49), specifically immunoprecipitated by C3, among the expression products in GC 26.

There is also shown in FIG. 7 the diagrammatic structure of the plasmid pFS-1019, as it has been obtained by:

digestion of plasmid pSW-119 or pFS-119 separation by electrophoresis of the fragments obtained on agarose gel, selection according to fragment sizes of that of the fragments derived from pSW-119 or pCW-119 and having the size of the latter, reduced however by about 315 pairs of bases. In the same way the small fragment of 315 pairs of bases XbaI-XbaI, was collected, also obtained from the digestion medium under the same conditions.

The first fragment selected was recircularied by means of a ligase, to form the plasmid pFS 1019. After incorporation of that plasmid in *E. coli* 1106, the latter led to the obtaining of a truncated fusion protein of 39,000 daltons, which is no longer recognized by monoclonal antibody CD-VP1 or C3.

On the contrary, the small fragment 315 nucleotide bounded by XhaI ends leads, after reintroduction thereof in phase into a gene carried by a suitable plasmid, to a modified plasmid capable of transforming *E. coli* 1106, thereby rendering the latter capable of expressing a hybrid protein recognized by the monoclonal antibodies C3. For example, this reintroduction in phase can be carried out in the gene of $\beta$-lactamase of pBR-322.

The placing in appropriate phase may, if necessary, be carried out by the technique described in French patent application no. 78 32041 of 13 Nov. 1978.

The reinsertion of the fragment XbaI-XbaI, whatever its origin, in plasmid pFS 1019 leads again to a plasmid of which the expression products contain a protein recognizable by C3. It has been so, particularly as concerns plasmid pCW 119, which was obtained by reinsertion in the site XbaI of pFS 1019 of a fragment XbaI-XbaI of the same size and nucleotide structure, isolated from pPV1-366 also described in the patent application 81 09 968.

The nucleotide sequence of the fragment XbaI-XbaI (315 pairs of nucleotides) has already been indicated above. Peptide sequence of the peptide Ser 23- Ser 128 was indicated too hereabove.

In FIG. 9 there is represented a diagram of plasmid pCW 119, in which the sequence coding for the VP 1 protein has been represented by a hatched area bounded by two circular arcs. The principal sites contemplated within the scope of the present description are also indicated in FIG. 9.

The determination and obtaining of smaller peptide sequences capable of bearing the immunogenic site sought (or epitope recognized by C3) were conducted in the following manner.

Plasmid pCW 119 was subjected to digestion with the restriction enzyme Kpn I, which opened it at the level of the restriction site 3064 (consequently outside the abovesaid fragment XbaI). The utilization of the above-defined process, bringing into play repeated trimming cycles with the enzyme Bal 31, led to the loss of successive end fragments, including those coding for the abovesaid sequences "His 65-Phe 105" and "Asp 93-Leu 104". The deletion from the linearized plasmids of the fragments containing the sequences coding for the peptide sequences which have just been mentioned, was manifested by the loss by the plasmid subsequently recircularized (by means of T4-DNA-ligase) of its capacity to induce the production in bacteria transformed by it, of peptide sequences capable of being recognized by the monoclonal antibodies CD-PV1 or C3.

In order to localize with still more accuracy the epitope recognized by C3, a series of plasmids derived from pCW 119 and including more or less extensive deletions of the related sequence were constructed. The relative positions of the fragments deleted with respect to the sites XbaI (2546) and (2861) are shown diagramatically by the circular arcs appearing in FIG. 9. The limits of these deletions to the left have been determined by linearization of the plasmids (on 1 $\mu$g of DNA) with XbaI and after treatment with Klenow's enzyme for one hour at 15° C., and labelling in the presence of [$\alpha^{32}$p]-dATP (10 $\mu$Ci) and of dGTP, dCTP and dTTP (in proportions of 0.2 mM of each of the latter constituents). The labelled DNA was then digested by means of the restriction enzymes indicated below (conditions of partial digestion when AluI is used). The labelled restriction fragments were then separated on a 5% polyacrylamide gel and made visible by autoradiography. The limits of the deletions towards the right have been deduced from the sizes of the deleted fragments and confirmed by the presence or absence of restriction sites for the enzymes identified in the upper portion of FIG. 10. The symbols used in the latter have the following meanings: X=XbaI; H=HhaI; A=AluI; S=Sau3A; K=KpnI; P=PstI. The numbers indicated correspond to the positions of the nucleotides concerned with respect to FIG. 8.

The truncated fusion proteins expressed by the plasmids pCW217, 213, 215, and 202 still react with the neutralizing C3 monoclonal antibody. To the contrary, the truncated fusion proteins expressed by the plasmids pCW216, 203, 218 and 223 are no longer recognized by the antibody C3. Accurate mapping by restriction enzymes has enabled it to be determined that the largest deletion which did not affect the reactivity of the truncated protein with C3 (pCW215) extended up to nucleotide 2792

(Leu)
104 and that the smallest deletion manifested by a loss of activity of truncated proteins extends up to nucleotides 2771-2782

(Thr—Lys)
98  108 under the experimental conditions which have been used.

Consequently, it may be considered that the C-terminal end of the amino acid sequence constituting a neutralizing epitope recognized by C3 is located between the amino acids 95, 110, and more particularly still between amino acids 98 and 104 of the VP1 protein. This region corresponds also to a hydrophilic zone of the protein.

INSERTION OF THESE DNA SEQUENCES IN AN EXPRESSION VECTOR

The sequence XbaI-XbaI includes neither an initiation codon, nor a termination codon. Neither does it include a promoter for its transcription, nor a signal of recognition by ribosomes (sequences of SHINE and DALGARNO, described in GIRARD and HIRTH, Virologie Moléculaire, Edition Doin 1980, pp. 15–46 and 263–264). To achieve expression of said sequence it must be inserted in phase within the nucleotide sequence, preferably in the middle thereof, (and in any case behind the initiation AUG) of a gene cloned with its promoter (or a foreign promoter linked thereto upstream of said gene). The use of linkers, as described above, enables the use of several different types of expression vectors to be envisaged according to the promoter concerned for example of the type indicated below by way of example.

a) Bacterial Promoters

They are particularly suitable in connection with plasmids containing the promoter-operator region of the lactose operon of *E. coli* (operon lac), followed by the portion 5′ of the gene of β-galactosidase. These vectors, of the type pPC (CHARNAY et al, Nucleic Acid Research 1978, tome V, pp. 4479–4494), enable the insertion of the sequence at the EcoRI site situated at 21 nucleotides behind the initiation AUG of β-galactosidase. The protein to which they give birth includes therefore for the N terminal end, the seven (or eight) first amino acids of bacterial β-galactosidase, followed by amino acids coded by the sequence of the mutation b) Phage Promoters They are particularly suitable in connection with plasmids containing the promoter-operator region of the left operon ($P_L$) or of the right operon ($P_R$) of the phage λ. These vectors, respectively of the type pKC30 (ROSENBERG, Nature 1981, vol. 292, p. 128) or pCL47 (ZABEAU and STANLEY, The EMBO Journal, 1982, vol. I, pp. 1217–1224) derived from pLK5 (or pRC5) and from pLG400, the latter being described in Cell, 1980, vol. 20, pp. 543–553, enable the insertion of said sequence to be effected into nucleotide sequences coding respectively for the N terminal end of the product of the N gene or for that of the product of the cro gene deposited 8 Feb. 1982 at the C.N.C.M. under no. I-184. These vector systems are propagated at 30° C. in bacteria lysogenised by a λ phage with thermosensitive repressor (cI 857) or in the presence of plasmids bearing the same gene (cI 857) coding for a thermosensitive repressor. They remain inactive, due to the action of the repressor, as long as the culture is kept at 30° C. The warming up of the culture to 42° C. is followed by the activation of the λ promoters ($P_L$ or $P_R$) borne by the recombinant plasmid, consequent to the inactivation of the repressor of the cI 857 gene.

c) Viral Promoters

They are particularly suitable when the SV40 is used as vector. In this case, the late viral promoter is used and the sequence of the poliovirus is inserted in place of all or part of the region coding for the late proteins of SV40 (VP1 or VP2). In this way substituted DNAs of SV40 are constructed in which the sequences coding for the capsid proteins of this virus are replaced by the sequence coding for the immunogenic peptide. Thus the insertion of said sequence, if need be through suitable linkers in place of the late fragment HaeII-PstI of SV40 (nucleotides from 767 to 1923), or of a portion of this fragment, results in the creation of a chimeric gene possessing a sequence coding for an immunogenic peptide inducing in vivo antibodies active with respect to poliovirus directly downstream of the N terminal portion of the protein VP2 of SV40.

It is possible to proceed in the same way by substituting the VP1 sequence of the poliovirus for that of SV40 between the sites EcoRI (1718) and BamH1 (2469).

d) Promoters of animal viruses borne by bacterial plasmids

This applies in relation to plasmids bearing promoters of the gene of thymidine-kinase of the herpes virus (pAGO), of the gene of the HBs antigen of the virus of B hepatitis (pAC-2 or pAC-14) or of the early or late genes of adenovirus 2 etc. The insertion of an immunogenic sequence according to the invention behind the AUG of the viral gene cloned with its promoter enables the expression thereof in the animal cell to be ensured (after transfection, microinjection or cell-protoplast fusion).

The peptide sequences or "sequences according to the invention" are accessible by chemical synthesis, for example, by resorting to the one of the conventional process, the operation conditions of which are recalled hereafter.

The synthesis of peptides in homogeneous solution and in solid phase is well known.

In this respect, recourse may be had to the method of synthesis in homogeneous solution described by HOUBENWEYL in the work entitled "Methodem der Organischen Chemie" (Methods of Organic Chemistry) edited by E. Wünsch., vol. 15-I and II, THIEME, Stuttgart 1974.

This method of synthesis consists of successively condensing the successive aminoacyl groups, two by two in the required order, or to condense aminoacyl groups and fragments previously formed and containing already several aminoacyl residues in the appropriate order, or again several fragments previously prepared, it being understood that care will be taken to protect beforehand all the reactive functions borne by these aminoacyl groups or fragments with the exception of the amine functions of the one and the carboxyl of the other or vice versa, which must normally take part in the formation of the peptide bonds, particularly after activation of the carboxyl function, according to methods well known in the synthesis of peptides. As a variation, recourse may be had to coupling reactions bringing into play conventional coupling reagents, of the carbodiimide type. such as, for example, 1-ethyl-3-(3-dimethyl-aminopropyl)-carbodiimide. When the aminoacyl group employed possesses an additional amine function (case of lysine for example) or another acid function (case, for example, of glutamic acid), these functions will for example be protected by carbobenzoxy or t-butyloxycarbonyl groups, as regards the amine functions, or by t-butylester groups, as regards the carboxylic functions. Procedure will be similar for the protection of any other reactive function. For example, when of the aminoacyls concerned contains an SH function (for example cysteine), recourse will be had to an acetamidomethyl or paramethoxybenzyl group.

In the case of progressive synthesis, amino acid by amino acid, the synthesis starts preferably by the condensation of the C-terminal amino acid with the amino acid which corresponds to the neighboring aminoacyl group in the desired sequence and so on, step by step, up to the N terminal amino acid. According to another preferred technique of the invention, recourse is had to that described by R. D. MERRIFIELD in the article entitled "Solid phase peptide synthesis" (J. Am. Chem. Soc., 45, 2149-2154).

To prepare a peptide chain according to the MERRIFIELD process, recourse is had to a very porous polymeric resin, to which is fixed the first C-terminal amino acid of the chain. This amino acid is fixed to the resin through its carboxylic group and its amino function is protected, for example by the t-butyloxycarbonyl group.

When the first C-terminal amino acid is thus fixed to the resin, the protective group of the amine function is removed by washing the resin with an acid.

In the case where the protective group of the amine function is the t-butyloxycarbonyl group, it may be eliminated by treatment of the resin by means of trifluoroacetic acid.

Then the second amino acid which is to provide the second aminoacyl group of the desired sequence, from the C-terminal aminoacyl residue is coupled to the deprotected amine function of the first C-terminal amino acid fixed to the resin. Preferably, the carboxyl function of this second amino acid is activated, for example by dicyclohexylcarbodiimide, and the amine function is protected, for example by t-butyloxycarbonyl.

In this way the first part of the desired peptide chain is obtained, which comprises two amino acids, and of which the terminal amine function is protected. As previously, the amine function is deprotected, and it is then possible to proceed with the fixing of the third aminoacyl group, under conditions similar to those of the addition of the second C-terminal amino acid.

In this way, the amino acids, which will constitute the peptide chain, are fixed one after the other to the amine group each time deprotected previously of the portion of the peptide chain already formed, and which is attached to the resin.

When the whole of the desired peptide chain is formed, the protective groups of the different amino acids constituting the peptide chain are removed and the peptide is detached from the resin, for example, by means of hydrofluoric acid.

DETECTION OF THE EXPRESSION OF THE IMMUNOGENIC SEQUENCES ACCORDING TO THE INVENTION

The expression of recombinant plasmids bearing said immunogenic sequences and capable of expressing them, that is to say of effecting the synthesis of an immunogenic peptide, is detected by immunoprecipitation techniques, known in themselves and preferably bringing into play ascites liquids containing C3 monoclonal antibodies or anti-VP1 rabbit serum ($\alpha$ VP1).

As regards the sequences of smallest size and bearing an epitope or immunogenic determinant, and more particularly those which are accessible relatively easily by chemical synthesis, it will be desirable, in order to accentuate their in vivo immunogenic character, to couple or "conjugate" them covalently to a physiologically acceptable and non toxic carrier molecule.

By way of examples of carrier molecules or macromolecular supports which can be used for making the conjugates according to the invention, will be mentioned natural proteins, such as tetanic toxin, ovalbumin, albumin serum, hemocyanins, etc.

As synthetic macromolecular supports, will be mentioned, for example, polylysines or poly(D-L-alanine)-poly(L-lysine)s.

The literature mentions other types of macromolecular supports which can be used, which have generally a molecular weight higher than 20,000.

To synthesize the conjugates according to the invention, recourse may be had to processes known in themselves, such as that described by FRANTZ and ROBERTSON in Infect. and Immunity, 33, 193–198 (1981), or that described in Applied and Environmental Microbiology, October 1981, Vol. 42, no. 4, 611–614 by P. E. KAUFFMAN using the peptide and the appropriate carrier molecule.

In practice, there will advantageously be used as coupling agent, the following compounds, without limitation thereto: glutaric aldehyde, ethyl chloroformate, water-soluble carbodiimides (N-ethyl-N'(3-dimethylaminopropyl) carbodiimide. HCl), diisocyanates, bis-diazobenzidine, di- and trichloro-s-triazines, cyanogen bromides, benzaquinone, as well as coupling agents mentioned in Scand. J. Immunol., 1978, vol. 8, p. 7–23 (AVRAMEAS, TERNYNCK, GUESDON).

It is possible to make use of any coupling process bringing into play, on the one hand, one or several reactive functions of the peptide and, on the other hand, one or several reactive functions of the support molecules. Advantageously, carboxyl and amine functions are involved, which can give rise to a coupling reaction in the presence of a coupling agent of the type used in the synthesis of proteins, for example, 1-ethyl-3-(3-dimethylaminopropyl)carbodiimide, N-hydroxybenzotriazole, etc. It is possible also to resort to glutaraldehyde, particularly when it amounts to coupling together amine groups respectively borne by the peptide and the support molecule.

Below is mentioned by way of example the coupling of the peptide Asp 93-Leu 104 to a support molecule constituted by the hemocyanin, particularly KLH, i.e. "Keyhole limpet hemocyanin" by means of glutaraldehyde by the method described by BOQUET, P; et Coll. (1982) Molec. Immunol., 19, 1541–1549. The coupling is done from proportions of about 2 mg of peptide per 2.25 mg of hemocyanin.

The conjugate obtained is immunoprecipitable by C3 monoclonal antibodies. This immunoprecipitation may be followed by labelling the conjugate with $^{125}$I using chloramine T. Given that the peptide does not contain tyrosine residues, the labelling only intervenes at the level of the support protein, so that the antigenic properties of the peptide could not be modified.

The immunogenicity of these peptides can also be reinforced, by producing their oligomerisation, for example, in the presence of glutaraldehyde or any agent enabling the bringing into play of coupling of distinct reactive functions borne by each of the monomeric peptides; in particular, the invention relates to the water soluble immunogenic oligomers thus obtained, comprising particularly from 2 to 10 monomer units.

In general, the invention relates to all small "immunogenic peptides" containing less than 20 aminoacyl residues, preferably less than 15 aminoacyl residues. These immunogenic peptides contain preferably the above indicated sequence Asp 93-Leu 104 or any sequence having a similar conformational structure.

The invention is naturally not limited to the particular peptides which have been envisaged.

As is well known to the technician skilled in the art, certain aminoacyl residues contained in the sequences concerned may possibly be replaced by other aminoacyl residues, to the extent that the latter do not substantially modify the surface configurations of the peptides formed, and their aptitude, particularly after their coupling with the macromolecular support, to react with antibodies directed against poliviruses. In this respect, will be mentioned, for example, the the possible substitutions of the alanyl group by the glycyl group or viceversa, the possible substitution of the iso-asparagic residues by aspartic, glutamine or isoglutamine residues, the substitution of valine groups by alanine, leucine or glycine groups, the substitution of lysine groups by norleucine groups or again arginine, etc., provided that each time the capacity of the modified peptides to induce antibodies capable of neutralizing the whole poliovirus or of being recognized by the CD-VP1 monoclonal antibodies, is verified. It is naturally understood that all these possible equivalents come within the field of the appended claims.

PROPERTIES OF THE PEPTIDES ACCORDING TO THE INVENTION

The peptides according to the invention, more particularly the conjugated peptides formed, are capable of inducing in vivo the production of antibodies by conventional techniques. It is possible to cause them to react with antipoliovirus antibodies. They induce the synthesis of antipoliovirus antibodies, when they are inoculated in the animal.

In addition it is possible to use them as reagents for the diagnosis and titration of antipoliomyelitic antibodies. In their use as reagents for a diagnosis, it is possible to resort to conventional techniques, for example, the ELISA technique. The principle of such a method is recalled below. It comprises, for example, the following steps:

deposition of certain amounts of the peptide according to the invention in the wells of a microplate of the type used for the practising of the ELISA method;

introduction of increasing dilutions of the serum containing, as the case may be, the antibodies to be detected or to be assayed, in the wells of this microplate;

incubation and interruption of the reaction, for example by the addition of a sulfuric acid solution;

thorough washing of the microplate with a suitable buffer;

introduction of labelled antibodies directed against the first, the labelling being done by means of an enzyme capable of hydrolising a substrate selected from among those for which this hydrolysis is evidenced by a variation in absorbance of a radiation of given wave length, measurement of the absorbance variation and determination, preferably with respect to similar measurements done with respect to a control, of the antibody content of the serum under study.

The DNA sequences according to the invention may themselves be used as hybridation probes enabling the detection of the presence of viral RNA or of the corresponding cDNA in a biological sample. This method involves, consequently, the prior extraction of the RNA or DNA from the biological sample and its contacting under conditions enabling hybridation with the DNA sequence according to the invention labelled by a radioactive tracer or by an enzyme, particularly of the type of those which are suited to hydrolyse a substrate of the above indicated type.

The invention relates naturally to all equivalent DNA sequences leading to expression products endowed with equivalent immunological properties, in that the antibodies induced by the expression products of these equivalent sequences capable of reacting with the expression products of the DNA fragments more particularly described and vice versa. In particular, the invention extends to DNA sequences which can differ from those which have been more particularly described, by deletions, additions or substitutions of nucleic acids, although the immunological properties of the expression products may be equivalent.

The invention also relates to a process for obtaining an immunogenic peptide such as described above comprising the steps which are the insertion of the DNA sequence according to the invention in a suitable vector, the transformation of a micro-organism transformable by the thus modified vector and capable of expressing the above said insertion sequence, the recovery of the proteins synthesized and the isolation of the peptide fraction containing the peptide according to the invention, the latter being detectable, if appropriate after fractionation dependent on molecular weights, by antibodies both against "C" and "D" particles of the same poliovirus and against the VP-1 structural poliopeptide of the capsid of this poliovirus.

The invention relates naturally also to any vector containing an insertion sequence according to the invention, under the control of a promoter enabling the expression of this insert in a micro-organism transformable by this vector.

Finally the invention relates to micro-organisms transformed by such a vector, adapted to produce a protein recognized by antibodies active, both against "C" and "D" particles of the same poliovirus and against the VP-1 structural polypeptide of the capsid of this polio-virus.

As is self-evident and as results besides from the foregoing already, the invention is in no way limited to those of its types of application and embodiments which have been more especially envisaged; it encompasses on the contrary all modifications, particularly those consisting of the corresponding peptide sequences derived from other poliovirus strains, whether these are type 1 strains or again type 2 or 3 strains. By way of example, will be mentioned the corresponding sequences (or equivalents) of the DNA coding for the protein VP1 of the Sabin strain. The peptide sequence of the Sabin strain which corresponds to the sequence His 65 -Ala 106 of VP-1 in the Mahoney strain, is distinguished from the latter by distinct aminoacyl residues at the positions indicated by the numbers indicated below:

88 (Ala), 90 (Ile), 95 (Ser), 98 (Lys) and 106 (Thr instead of Ala).

It is self-evident that the peptides which comprise the different amino acid substitutions which have been envisaged, constitute equivalents of those more specifically defined in the claims. These peptides are therefore, as such, also protected by the claims.

We claim:

1. A double-stranded DNA which comprises a DNA replica of a sequence of the poliovirus RNA, free of other DNA replica of other poliovirus RNA, which first mentioned replica contains at the most 315 pairs of nucleotides, which sequence codes for a peptide which can be recognized by antibodies active both against "C" and "D" particles of a poliovirus and against the VP-1 structural polypeptide of the capsid of poliovirus, said peptide comprising the amino acid sequence:

Asp Asn Pro Ala Ser Thr Thr Asn Lys Asp Lys Leu.

2. The DNA of claim 1 which consists of a DNA fragment characterized by the structural sequence:

TCT AGA GAC GCT CTC CCA AAC ACT GAA
GCC AGT GGA CCA ACA CAC TCC AAG GAA ATT
CCG GCA CTC ACC GCA GTG GAA ACT GGG GCC
ACA AAT CCA CTA GTC CCT TCT GAT ACA GTG
CAA ACC AGA CAT GTT GTA CAA CAT AGG TCA
AGG TCA GAG TCT AGC ATA GAG TCT TTC TTC
GCG CGG GGT GCA TGC GTG ACC ATT ATG ACC
GTG GAT AAC CCA GCT TCC ACC ACG AAT AAG
CAT AAG CTA TTT GCA GTG TGG AAG ATC ACT
TAT AAA GAT ACT GTC CAG TTA CGG AGG AAA
TTG GAG TTC TTC ACC TAT TCT.

3. The DNA of claim 1 which comprises less than 315 pairs of bases and which contains the nucleotide sequence coding for the amino acid sequence:

His Val Val Gln His
Arg Ser Arg Ser Glu Ser Ser Ile Glu Ser
Phe Phe Ala Arg Gly Ala Cys Val Thr Ile
Met Thr Val Asp Asn Pro Ala Ser Thr Thr
Asn Lys Asp Lys Leu Phe.

4. The DNA of claim 3 which contains the nucleotide sequence coding for the amino acid sequence:

His Val Val Gln His
Arg Ser Arg Ser Glu Ser Ser Ile Glu Ser
Phe Phe Ala Arg Gly Ala Cys Val Thr Ile
Met Thr Val Asp Asn Pro Ala Ser Thr Thr
Asn Lys Asp Lys Leu Phe Ala Val Trp Lys
Ile.

5. The DNA of claim 1 which is a recombinant DNA containing said poliovirus DNA replica.

6. The DNA of claim 5 which consists of a vector in which said poliovirus DNA replica forms an insert placed under the control of a promoter present in said vector and enabling the expression of this insert in a cell transformed by this vector.

7. The DNA of claim 5 wherein said insert has the nucleotide sequence:

TCT AGA GAC GCT CTC CCA AAC ACT GAA
GCC AGT GGA CCA ACA CAC TCC AAG GAA ATT
CCG GCA CTC ACC GCA GTG GAA ACT GGG GCC
ACA AAT CCA CTA GTC CCT TCT GAT ACA GTG
CAA ACC AGA CAT GTT GTA CAA CAT AGG TCA
AGG TCA GAG TCT AGC ATA GAG TCT TTC TTC
GCG CGG GGT GCA TGC GTG ACC ATT ATG ACC
GTG GAT AAC CCA GCT TCC ACC ACG AAT AAG
CAT AAG CTA TTT GCA GTG TGG AAG ATC ACT
TAT AAA GAT ACT GTC CAG TTA CGG AGG AAA
TTG GAG TTC TTC ACC TAT TCT.

8. The DNA of claim 5 in which said insert comprises less than 315 pairs of bases and which contains the nucleotide sequence coding for the amino acid sequence:

His Val Val Gln His
Arg Ser Arg Ser Glu Ser Ser Ile Glu Ser
Phe Phe Ala Arg Gly Ala Cys Val Thr Ile
Met Thr Val Asp Asn Pro Ala Ser Thr Thr
Asn Lys Asp Lys Leu Phe.

9. The DNA of claim 5 in which said insert comprises less than 315 pairs of bases and which contains the nucleotide sequence coding for the amino acid sequence:

His Val Val Gln His
Arg Ser Arg Ser Glu Ser Ser Ile Glu Ser
Phe Phe Ala Arg Gly Ala Cys Val Thr Ile
Met Thr Val Asp Asn Pro Ala Ser Thr Thr
Asn Lys Asp Lys Leu Phe Ala Val Trp Lys
Ile.

10. A microorganism transformed by a vector containing an insert consisting of a DNA sequence according to any one of claims 1 to 4 or 5 under the control of a promoter enabling the expression of this insert in a microorganism transformed by this vector, and capable of expressing the protein encoded by said insert.

11. A process for the preparation of a polypeptide having the sequence

Ser Arg Asp Ala Leu Pro Asn Thr Glu
Ala Ser Gly Pro Thr His Ser Lys Glu Ile
Pro Ala Leu Thr Ala Val Glu Thr Gly Ala
Thr Asn Pro Leu Val Pro Ser Asp Thr Val
Gln Thr Arg His Val Val Gln His Arg Ser
Arg Ser Glu Ser Ser Ile Glu Ser Phe Phe
Ala Arg Gly Ala Cys Val Thr Ile Met Thr
Val Asp Asn Pro Ala Ser Thr Thr Asn Lys
Asp Lys Leu Phe Ala Val Trp Lys Ile Thr
Tyr Lys Asp Thr Val Gln Leu Arg Arg Lys
Leu Glu Phe Phe Thr Tyr Ser.

or fragments thereof and which polypeptide or fragment can be recognized by monoclonal antibodies active both against particles "C" and "D" originating from a poliovirus and against the structural polypeptide VP-1 of the capsid of a poliovirus, said polypeptide containing not more than 105 amino acids, which comprises inserting a DNA sequence coding for said polypeptide in a suitable vector, transforming a microorganism transformable by said vector, with said vector after insertion therein of said DNA sequence, recovering expression products of said transformed microorganism, including the polypeptide coded by said DNA sequence, fractionating the polypeptides expressed and contacting the fractions with antibodies active both against "C" and "D" particles of a poliovirus and against the VP-1 structural polypeptide of the capsid of this poliovirus and recovering the polypeptide which reacted with said antibodies.

* * * * *